(12) United States Patent
Reilly et al.

(10) Patent No.: US 10,029,056 B2
(45) Date of Patent: Jul. 24, 2018

(54) SYSTEM AND METHOD FOR MONITORING USE OF A DEVICE

(71) Applicants: THE PROVOST, FELLOWS, FOUNDATION SCHOLARS, & THE OTHER MEMBERS OF BOARD, OF THE COLLEGE OF THE HOLY & UNDIV. TRINITY OF QUEEN ELIZABETH NEAR DUBLIN, Dubin (IE); ROYAL COLLEGE OF SURGEONS IN IRELAND, Dublin (IE)

(72) Inventors: Richard Reilly, Dublin (IE); Richard Costello, Dublin (IE); Cian Hughes, Dublin (IE); Ehsan Chah, Dublin (IE); Isabelle Killane, Dublin (IE)

(73) Assignees: The Provost, Fellows, Foundation Scholars, & The Other Members of Board, of the College of the Holy & Undivided Trinity of Queen Elizabeth near Dublin, Dublin (IE); Royal College of Surgeons in Ireland, Dublin (IE)

(*) Notice: Subject to any disclaimer, the term of this patent is extended or adjusted under 35 U.S.C. 154(b) by 589 days.

(21) Appl. No.: 14/424,964

(22) PCT Filed: Aug. 29, 2013

(86) PCT No.: PCT/EP2013/067932
§ 371 (c)(1),
(2) Date: Feb. 27, 2015

(87) PCT Pub. No.: WO2014/033229
PCT Pub. Date: Mar. 6, 2014

(65) Prior Publication Data
US 2015/0231343 A1 Aug. 20, 2015

Related U.S. Application Data

(60) Provisional application No. 61/694,416, filed on Aug. 29, 2012.

(30) Foreign Application Priority Data

Aug. 29, 2012 (EP) .................................... 12182189

(51) Int. Cl.
*A61M 15/00* (2006.01)

(52) U.S. Cl.
CPC ...... *A61M 15/0033* (2014.02); *A61M 15/002* (2014.02); *A61M 15/0048* (2014.02);
(Continued)

(58) Field of Classification Search
CPC .............. A61M 15/002; A61M 15/003; A61M 15/0048; A61M 15/0065; A61M 15/0068;
(Continued)

(56) References Cited

U.S. PATENT DOCUMENTS 5,331,953 A * 7/1994 Andersson ............ A61M 15/00
128/200.14
2011/0290240 A1 12/2011 Meyer et al.
(Continued)

FOREIGN PATENT DOCUMENTS

EP 0 387 222 A1 9/1990
GB 2 395 437 A 5/2004
(Continued)

OTHER PUBLICATIONS

Sovijarvi, Anssii R.A. et al. "Averaged and Time-Gated Spectral Analysis of Respiratory Sounds: Repeatability of Spectral Parameters in Healthy Men and in Patients with Fibrosing Alveolitis", CHEST, vol. 109, No. 5, May 1, 1996, pp. 1283-1290.
(Continued)

*Primary Examiner* — Lynne Anderson
(74) *Attorney, Agent, or Firm* — K&L Gates LLP

(57) ABSTRACT

A system and method suitable for monitoring user technique of an inhaler device configured for delivery of a medicament is provided. The system may include a microphone adapted for sensing sound made during operation of the inhaler device and processing circuitry operable to process a data signal obtained from the microphone, wherein the data signal includes acoustic information sensed. The processing circuitry is adapted to determine inhalation and exhalation breath characteristics that occur during use, by analyzing the temporal and spectral components of the acoustic information sensed and processed to differentiate between an inhalation and an exhalation, based on both the temporal and spectral components. This information can be processed to determine user technique adherence to inhaler or respiratory device protocol. The analysis of temporal and spectral components can determine the impact of user technique errors on the quantity and the deposition of medicament delivered into the user's airways.

19 Claims, 10 Drawing Sheets

(52) U.S. Cl.
CPC ..... *A61M 15/0065* (2013.01); *A61M 2205/18* (2013.01); *A61M 2205/3303* (2013.01); *A61M 2205/3334* (2013.01); *A61M 2205/3375* (2013.01); *A61M 2205/3379* (2013.01); *A61M 2205/42* (2013.01); *A61M 2205/52* (2013.01); *A61M 2230/40* (2013.01)

(58) Field of Classification Search
CPC ............ A61M 15/008; A61M 15/0083; A61M 15/0091; A61M 2205/18; A61M 2205/3303; A61M 2205/3334; A61M 2205/3375; A61M 2205/52
See application file for complete search history.

(56) References Cited

U.S. PATENT DOCUMENTS

| | | | |
|---|---|---|---|
| 2013/0151162 A1* | 6/2013 | Harris | A61M 15/00 702/19 |
| 2014/0257126 A1* | 9/2014 | Vink | A61M 15/0086 600/529 |

FOREIGN PATENT DOCUMENTS

| | | |
|---|---|---|
| WO | 2007/101438 A1 | 9/2007 |
| WO | 2011/083377 A1 | 7/2011 |
| WO | 2011/135353 A1 | 11/2011 |

OTHER PUBLICATIONS

Aucouturier et al. "Segmentation of expiratory and inspiratory sounds in baby cry audio recordings using hidden Markov models," The Journal of Acoustical Society of America, Nov. 1, 2011, pp. 2969-2977.

International Search Report and Written Opinion dated Nov. 28, 2013 for PCT/EP2013/067932 (13 pages).

* cited by examiner

SYSTEM AND METHOD FOR MONITORING USE OF A DEVICE

CROSS REFERENCE TO RELATED APPLICATIONS

This application is the U.S. National Phase of International Application No. PCT/EP2013/067932, filed Aug. 29, 2013, designating the U.S. and published as WO 2014/033229 on Mar. 6, 2014 which claims the benefit of European Patent Application No. 12182189.6, filed Aug. 29, 2012 and U.S. Provisional Patent Application No. 61/694,416, filed Aug. 29, 2012.

Any and all applications for which a foreign or domestic priority claim is identified above and/or in the Application Data Sheet as filed with the present application are hereby incorporated by reference under 37 CFR 1.57.

FIELD OF THE INVENTION

The invention relates to a monitoring device and method for monitoring use of a device. In particular the invention relates to monitoring the correct use of drug delivery and inhaler devices.

BACKGROUND TO THE INVENTION

Most chronic respiratory and nasal diseases, as well as some systemic diseases are treated with inhaled medications. However, a problem with giving medications via inhalers is that patients often do not take their medication as directed. Non-adherence to medication regimes refers to missing doses of medication, incorrect technique when using the inhaler and potentially over medicating. Non-adherence is a major problem rooted in a lack of understanding about medication and a misunderstanding of directions for use. For inhaled medication, adherence involves both using the inhaler at the correct time of day (temporal adherence) and in the correct manner (technique adherence). Rates of non-adherence amongst asthma patients alone range from 30% to 70%. The detection of when and how an inhaler is used by analysing acoustic recordings of inhaler usage can provide evidence about patients' adherence to their inhaled medication regime. Manually listening to acoustic recordings of inhaler usage to assess adherence is a tedious and time consuming process and thus a device or system which can automatically and accurately carry out this task would be of great value.

There are a number of challenges associated with analysing patient inhaler technique through the use of acoustics in uncontrolled environments. Often great quantities of artefacts are generated by the patient or the background environment in which the patient uses their inhaler. In many cases it has been found that patients unintentionally exhale into the mouthpiece of an inhaler, dispersing some or even all of the medication. There are many systems that attempt to use acoustic information to analyse flow rates in terms of inhaler performance.

One such system is disclosed by UK patent publication number GB 2 395 437, assigned to Profile Respiratory Systems, that discloses a system which employs sensors to identify sounds in the operation of the device and primarily associated with investigating flow rates in terms of inhaler performance, however the system does not effectively identify errors in inhaler operation.

Another system is disclosed by PCT patent publication number WO2011/135353, assigned to Sagentia Limited, which discloses a drug delivery device that includes sensors and processing circuitry that can detect operating events, such as flow rates and drug delivery, in various types of inhalers, such as dry powder inhalers, metered dose inhalers, nasal inhalers and nebulisers. The information determined by the processing circuitry can be used to provide feedback to the user or can be stored or transmitted for subsequent analysis. However a problem with this approach is that errors in technique are not identified. After manually classifying several hundred audio recordings of inhaler use, from a wide range of people, it is evident that there are a large number and variety of possible user technique errors. The Sagentia product identifies if the peak inhalation flow profile, as mandated by the manufacturers, is achieved. However if the patient has exhaled into the inhaler before inhalation the dose of the drug available will be reduced, potentially resulting in a missed dose. Exhalations into the device can disperse the drug and introduce a source of humidity to the inhaler. The hydrotropic nature of the drug means that it is likely to combine with the water vapour and clump in the device. This can lead to over dosing in subsequent inhalations. Other user errors include not holding one's breath for the required duration after an inhalation and improper inhalations such as short repeated inhalations instead of one long continuous inhalation.

Other systems in the art include WO2011/083377, assigned to Philips Electronics; EP 0 387 222, Draco AB; and US2011/290240, Meyer Adam et al, that identify one technique error, namely flow rate to achieve correct flow profile, however these systems inherently suffer from the same problems described above.

It is therefore desirable to provide an automatic detection system and method which is able to identify the full drug protocol, or lack of, when using an inhaler. This includes, recording the number doses of medication taken, the timing of these doses and the adherence to the prescribed usage protocol for that inhaler.

It is an object of the invention to provide a device which can record pertinent acoustic information surrounding inhaler use and one that provides valuable information regarding patients' adherence to their medication.

SUMMARY OF THE INVENTION

According to the invention there is provided, as set out in the appended claims, system suitable for monitoring user technique of an inhaler device configured for delivery of a medicament, said system comprising:
  a microphone adapted for sensing sound made during operation of the inhaler device;
  processing circuitry operable to process a data signal obtained from the microphone, wherein said data signal comprises acoustic information sensed,
  the processing circuitry is adapted to determine inhalation and exhalation breath characteristics that occur during use, by analysing the temporal and spectral components of the acoustic information sensed and processed to differentiate between an inhalation and an exhalation, based on both the temporal and spectral components.

There are a number of unique aspects of the invention: the use of acoustic signals to interpret how the inhaler is used through the combination of timing information and quantitative measures of the effectiveness of inhaler technique. It will be appreciated that in the context of the present invention that the invention can be used to analyse information from any type of inhaler device or respiratory device. Other devices use mechanical methods to assess inhalation power with no record of inhaler use. They also do not provide a record of how well a patient was at using their inhaler over certain time durations in order to inform the clinician of consistent problems. The data processing function of the invention can be performed on the inhaler device or on a separate processing device, such as a standalone personal computing device, or shared between devices depending on how the data processing function is configured.

The recordings of inhalation, associated with the use of the inhaler can be used to directly infer the patient's lung function and response to treatment. In particular, changes in inhalation volume over the course of treatment are related to acoustic features of inhalation, including acoustic energy, maximal and median amplitude, rising time of amplitude, duration of inhalation. Also exhalation features, recorded when the patient exhales relate to the degree of airflow limitation. Also, based on direct evidence the device can inform the user and others about the health of the patient through information on lung capacity and air flow, clinical changes in response to the medicines. Finally, the device can give information on several aspects of cognition, including executive cognitive function.

In one embodiment the processing circuitry further comprises means for identifying drug priming or blistering characteristics of the device to identified that a medicament is about to be delivered before an inhalation.

In one embodiment the drug priming characteristics comprises an acoustic signal generated by a mechanism, for example a lever, adapted to release the medicament that generates a unique energy profile of the lever movement convolved with the noise of blistering a capsule to release the medicament.

In one embodiment analysis of the temporal components provides an indicator of temporal adherence indicating correct volume of medication is delivered at the correct temporal intervals.

In one embodiment the system is adapted to be re-configured for different temporal adherence requirements depending on the device and medicament to be used.

In one embodiment there is provided means for identifying multiple inhalations; or an exhalation before inhalation after blistering of the capsule.

In one embodiment there is provided means for identifying insufficient inhalation volume to release the medication or delivery of the correct volume of the medication after blistering of the capsule.

In one embodiment the processing circuitry comprises means to identify different frequency components to differentiate between inhalations and exhalations.

In one embodiment the device comprises means for comparing a singular value decomposition of the short term power spectrum of the signal to a predefined threshold to identify potential breath sounds. The zero crossing rate of the breath sounds is compared to a predefined threshold to confirm these as breath sounds using said comparing means.

In one embodiment the signal is processed to determine the frequency domain components of the identified breath sounds and means for classifying detected sounds as an inhalation or an exhalation.

In one embodiment the processing circuitry comprises means for tracking time of device inhaler use for adherence analysis.

In one embodiment there is provided means for calculating the median amplitude and duration of an identified inhalation to determine the amount of medicament released from the device.

In one embodiment there is provided means for calculating the amplitude of an identified exhalation in order to determine if the medicament has been dispersed from the inhaler, before inhalation has occurred.

In one embodiment there is provided means to calculate the minimum energy to disperse the medicament that has been achieved at exhalation.

In one embodiment there is provided means to calculate the duration of any breath sound.

In one embodiment there is provided means for recording and storing a time stamp indicating when the device is used.

In one embodiment the device comprises an gyroscope adapted to identify that the inhaler device is being held in the correct plane in use. The gyroscope ensures the inhaler is in the correct orientation when used.

In an MDI inhaler part of the protocol is to shake the device beforehand and this can be detected for correct protocol adherence by an accelerometer. In another embodiment the accelerometer can be used to detect unwanted shaking of the device, for example in a DPI device shaking of the device after it has been primed is undesirable as the drug will be dispersed.

In one embodiment the device comprises a thermistor adapted to identify the differentiation between inhalations and exhalations.

In one embodiment the device comprises means for recording after the inhaler is closed in order to identify exhalations after inhalation.

In one embodiment there is provided a second microphone adapted to determine inhalation or exhalation breath characteristics.

In one embodiment the device comprises memory means adapted to store information for subsequent use.

In one embodiment the device comprises a second microphone in line with the first microphone in order to differentiate between exhalations and inhalations In one embodiment there is provided means for uploading data from the device to a separate computing device using one or more of a physical memory card; a cable, for example using a USB connection; or a wireless connection, for example using a Bluetooth protocol.

In another embodiment of the invention there is provided an algorithm for processing the audio downloaded from the device. The algorithm processes the audio to confirm the inhaler has been used correctly. It does this by identifying events that determine whether the inhaler was used correctly or not, for example inhalations must be differentiated from exhalations to ensure the user has inhaled the drug. The movement of the lever must be identified to ensure the drug has been released. Not only does the algorithm identify the events but it identifies the order in which they occur as this has a direct affect on whether the inhaler event is successful or not. For example an exhalation before the blister occurs does not affect drug delivery but an exhalation after the blister of the medication has occurred can profoundly affect delivery of drug to the patient's lungs. The ability to identify exhalations after the mandatory holding of one's breath post inhalations is also unique in this invention. Recordings of the acoustics of exhalation not only confirm that the patient has held their breath for a sufficient period of time to allow for the correct delivery of the drug but it also allows for acoustic analysis that relates airway calibre such as the presence of wheeze signatures and the duration of exhalation.

The current system can carry out post-processing of the data offline and presents information about timing errors and technique errors in a visual display that can easily be read by a clinician or patient. This information is to be used to educate the patient on the proper manner in which to use their inhaler.

Non-adherence to medication and errors in inhaler use are the problems addressed by this invention. The timestamping of the audio files provides a record of each inhaler use, thus enabling the system to identify when the inhaler is being over/under used. The identification of events such as inhalation and exhalations enables identification of technique errors in subject's use of the inhaler. These errors can be equivalent to missed doses.

The invention keeps a record of each inhaler actuation and can report statistics on adherence to medication in terms of timing and errors. A clinician can observe any consistent errors being made by the patient and set out to educate them on the correct use of this device.

In a further embodiment there is provided inhaler device suitable for delivery of a medicament, said device comprising:
a body with a mouthpiece and a microphone adapted for sensing sound made during operation of the device;
processing circuitry operable to process a data signal obtained from the microphone, wherein said data signal comprises acoustic information sensed; and
the processing circuitry is adapted to determine inhalation and exhalation breath characteristics that occur during use.

In another embodiment there is provided computer implemented system for monitoring user technique of an inhaler device configured for delivery of a medicament, said system comprising:
a module or means for processing a data signal obtained from a microphone, wherein said data signal comprises acoustic information sensed, characterised by
a module or means for determining inhalation and exhalation breath characteristics that occur during use of the inhaler, by analysing the temporal and spectral components of the acoustic information sensed; and
a module or means for differentiating between an inhalation and an exhalation based on both the temporal and spectral components.

In a further embodiment there is provided a method for monitoring user technique of an inhaler device configured for delivery of a medicament, said method comprising:
processing a data signal obtained from a microphone, wherein said data signal comprises acoustic information sensed, characterised by the steps of:
determining inhalation and exhalation breath characteristics that occur during use, by analysing the temporal and spectral components of the acoustic information sensed; and
differentiating between an inhalation and an exhalation based on both the temporal and spectral components.

There is also provided a computer program comprising program instructions for causing a computer program to carry out the above method which may be embodied on a record medium, carrier signal or read-only memory.

BRIEF DESCRIPTION OF THE DRAWINGS

The invention will be more clearly understood from the following description of an embodiment thereof, given by way of example only, with reference to the accompanying drawings, in which:—

DETAILED DESCRIPTION OF THE DRAWINGS

Figure 1:
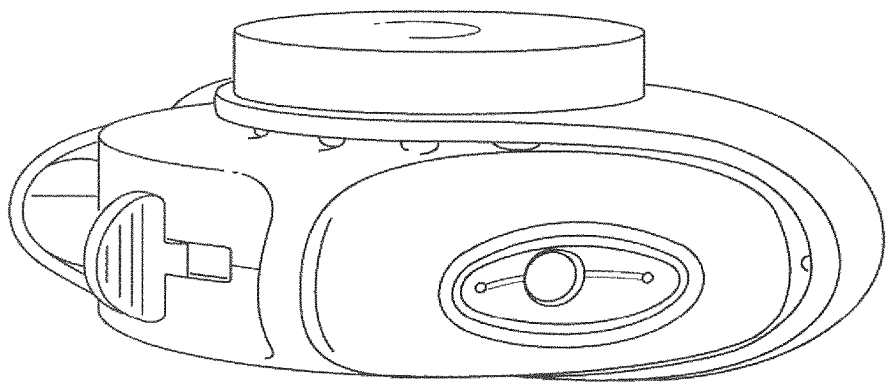
FIG. 1 illustrates an example inhaler device.

In one embodiment of the present invention FIG. 1 illustrates an inhaler device, for example a diskus inhaler. The inhaler comprises a system consisting of a microphone, a microprocessor, a battery and a memory means or card (not shown). The microprocessor is activated and begins recording each time the inhaler is opened. It will be appreciated that the system of the present invention can be embodied in an inhaler device or retrofitted to an existing inhaler device. The data can be uploaded to a remote location for subsequent post-processing that will be described in more detail below.

Figure 2:
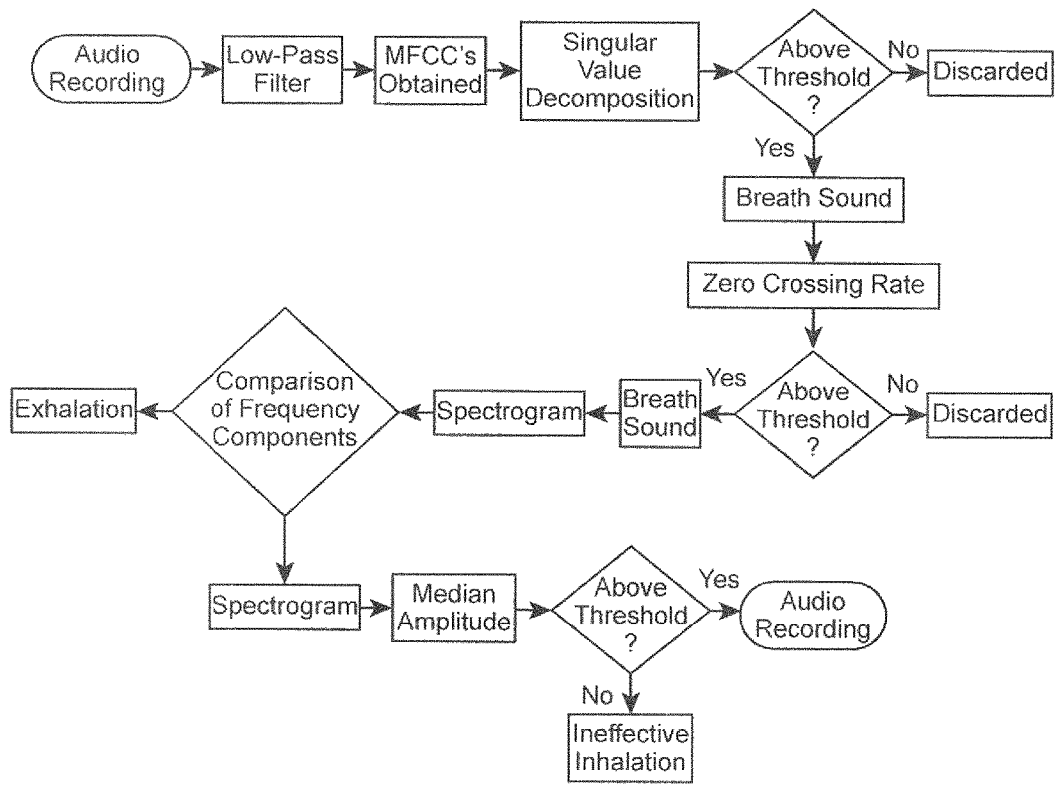
FIG. 2 illustrates a flow chart illustrating the steps of the processing circuit to identify breath sounds.

With reference to the flow chart of FIG. 2 the signal is processed to assess the operation of inhaler device by determining the existence and order of certain breath characteristics that can occur during inhaler use. A singular value decomposition of the short term power spectrum of the signal (Mel Frequency Cepstral coefficients (MFCCs)) is compared to a predefined threshold to identify potential breath sounds. The zero crossing rate of these breath sounds is also compared to a predefined threshold to confirm these as breath sounds.

The signal is then processed to determine the frequency domain components of the identified breath sounds to classify them as an inhalation or an exhalation. A ratio of the high and low frequency bands is employed to class each breath sound as an inhalation or an exhalation.

The signal is processed to identify the release of the drug by identifying the unique energy profile of the lever movement convolved with the noise of blistering the drug capsule.

The median amplitude and duration of the identified inhalation is calculated to determine the amount of drug released from the inhaler. The amplitude of the exhalation is also identified in order to determine if the drug has been dispersed from the inhaler, before inhalation has occurred.

The algorithm then uses this information to determine if a successful, partial or unsuccessful inhalation of the drug has been carried out. An inhaler event is classified as successful if the lever movement is identified and if a sufficient inhalation is present without a prior exhalation. A partial classification is given to an inhaler event if the median amplitude of the inhalation is below a threshold and/or a sufficient exhalation occurs before the inhalation and after the lever release. An unsuccessful classification will refer to an inhaler event where no inhalation has been identified.

Example Operation

A Knowles Acoustics SPM0204HE5 microphone was employed in the design as it has low power consumptions (250 µA), high sensitivity (42 dB±4 dB), low signal to noise ratio (59 dB) and it is physically very small (4.72 mm L×3.76 mm W×1.25 mm H). It will be appreciated any suitable microphone can be used. A microSD card, a serial interfaced NAND flash, is employed due to its relatively low power consumption (15 mA), small form factor, and removable nature.

A ⅟₁₀ D cell Lithium-Thionyl Chloride (Li—SOCl2) battery was chose as this chemistry allows for a high current draw relative to the battery's physical size, while still providing enough capacity to last for a month of operation and up to 24 months of device standby time prior to use.

The device can be turned on by triggering a switch and the microprocessor receives power, the firmware begins to execute and the device is activated. The device initially configures the internal and external clocks. Secondly the memory card can be initialised, this confirms correct function of the memory card, reads in the initial Real Time Clock (RTC) value, and sets the starting sector on the card at which the next recording will be written. The microcontroller has a 16-bit $\Sigma$-$\Delta$ analogue to digital convertor (ADC) with an internal reference. On start-up the firmware must configure the ADC. The ADC receives a clock signal from the microcontroller's internal digitally controlled oscillator, which is calibrated at 8 MHz. A 4-times clock divider reduces this speed to 2 MHz, this combined with an over sampling rate of 256 produces 7874 samples per second, which equates roughly to the 8 kHz target capture resolution originally specified for the device. While the ADC has a resolution of 16 bits, half of these are discarded and only the 8 most significant bits are recorded. This gives a data rate just under 64 kBits per second and audio quality comparable to an ISDN (digital fixed line) phone call, which is more than sufficient for analysis purposes.

When the inhaler device is subsequently opened by the user a magnetic reed switch is triggered and an interrupt request is raised, this wakes the device from low power mode, and triggers a function, which begins a new recording. Before a new recording may begin the device performs three integrity checks, firstly it ensures that the device is not already recording, secondly it checks that the RTC is operating correctly, and thirdly it checks that the card is operating correctly. The microprocessor continues recording until the inhaler is closed and the recording is saved to the memory card. The device then goes into low power mode to conserve battery power.

When the device is in low power mode the internal clocks stop to conserve power. During this time an external 32,768 Hz crystal oscillator keeps time. Once every second (every 32,768 cycles), a watch-dog timer triggers an interrupt in which an integer representing the time since the device was powered is incremented by one. Each time a recording begins this time stamp is stored as part of the recording's metadata. During a recording a watch-dog interrupt function increments a timer variable that monitors the recording length, if the recording length exceeds a pre-set length (currently 120 seconds), the recording will stop regardless of switch position in order to conserve battery power. This timer ensures that if an inhaler is accidentally opened or left open following use it will not continue to record indefinitely draining the limited battery capacity.

When the patient returns the device it is essential that the data can be easily read off the device. The SD card can be removed from the device, placed in a card reader and the data downloaded onto a desktop PC. Alternatively the data can be downloaded with a cable direct to a USB. From here it is uploaded to a web server over an encrypted link. Metadata from the device file is interpreted in order to calculate the times at which the inhaler was used.

An important aspect of the invention is the positioning of the hardware and firmware in the device design. In a first aspect the orientation of the microphone was changed to face down; this improved the fidelity of the audio recordings. Normally the placement of the microphone is facing upwards within the device and resulting in the recording of a significant amount of ambient noise. A second aspect of the invention was the replacement of the removable SD card to a solid state memory module. This reduced the processor noise involved in writing data to memory and improved the reliability of the memory module. The recording protocol has also changed slightly, the recording continues for 10 seconds after the inhaler is closed in order to record exhalation. Finally the manner in which the data is extracted from the device changed; the data is removed from the device via direct memory access and connection to USB.

The algorithm processes the audio signal recorded of each inhaler use to identify a selection of events that can be related to inhaler technique. Events to be identified are: inhalations, exhalations and lever movement.

Signal is filtered to remove all frequency elements about 1300 Hz

Signal segmented into frames of 700 ms.

Overlapping frame begins 20 ms after previous frame

Singular vector adaptive threshold set to 14% higher than lowest computed value.

Zero crossing rate threshold set to 0.002. This was found to reduce false positives through trial and error.

Breath events are identified from this process

Mean amplitude from these breath samples is extracted

Spectral density measurements are employed to differentiate between inhalations and exhalations Acoustic threshold values are employed to assess the likelihood of the breath phase in releasing drug from the inhaler A decision tree is employed to classify the overall inhaler event as Pass, Fail or Incomplete.

The output file is a text file containing information about the presence of inhaler events, when they occur relative to others and a classification of them in terms of the thresholds known for each type of event.

Output file changed to more user friendly presentation and for easier data import into Microsoft Excel.

After breath sounds have been identified from the above the algorithm sets to finding 'blow-ins' to the inhaler. Exhalations or 'blow-ins' are identified by examining the frequencies between 20-200 Hz. It has been found from observations that exhalations have a characteristic pattern in this frequency band. The power spectral density of the signal is calculated and subsequently converted into decibels. If the mean power of the signal is greater than a fixed threshold of 65 dB then it is labelled as an exhalation. The fixed threshold was calculated from empirical observations.

The same method is used to identify blister sounds. However this movement of the Diskus lever causes a distinctive pattern at high frequencies. Blisters can be identified through calculating the power spectral density in the 2000-3000 Hz frequency band. A fixed threshold of 77 dB, again set by empirical observations, was set with any section of the signal above this threshold classified as a blister event. An additional constraint was set in that a blister can only occur after 0.5 s of the Diskus inhaler being opened, any potential blister events which occur before this time are deemed as false positives.

From the identification of the events and their timing in relation to other events we can identify the following technique errors Blowing into device after lever movement and before inhalation Multiple inhalations less than 5 seconds apart No lever movement Double lever movement No/very weak inhalation Exhaling before five seconds after inhaling If any of these event are identified the algorithm will indicate that an error has occurred.

Finally a traffic light system can be displayed that has a light representing each inhaler event and the colour of the light represents whether it was correct in time and technique, if it was incorrect in time OR technique or if it was incorrect in time and technique. This information can highlight any consistent errors occurring in a patient's inhaler use.

It will be appreciated that the hardware and the software of the system can be modified to suit various inhalers and drug protocols according to their application.

Experimental Data

The relationship between acoustic energy and amount of drug dispersed in a Seretide Diskus DPI when an exhalation in the direction of the mouthpiece occurs is now described with respect to experimental data.

It is hypothesized that blowing into the mouthpiece of a Dry Powder Inhaler (DPI) such as the Diskus reduces the amount of drug available for inhalation, if the blister containing the drug has been previously pierced. Patients who inhale reduced amounts of medication prescribed are in danger of not receiving the full therapeutic effects anticipated. Investigating how the intensity of blowing into an inhaler can affect the amount of drug available for inhalation can provide empirical evidence regarding what level of exhalation is deemed detrimental. Patients using DPIs are advised to exhale normally but not towards or near the DPI (particularly the mouthpiece). Exhaling into a DPI can create two problems. Firstly the drug dose can be blown away. Secondly exhaling into a DPI can introduce humidity, which may cause the medication to clump together or attach to the side of the mouthpiece.

Exhalation until FRC (Functional Residual Capacity) is deemed sufficient prior to inhalation, as previous research has found that forced expiration is no more effective and is also likely to cause broncho spasm (i.e. coughing). The use of an improper technique with DPI's reduces the efficacy of the drugs (bronchodilators etc.) being administered. A critical error for all DPIs is blowing into the device before inhalation. However it should be noted that exhaling into a DPI would be of greater significance with bulk reservoir devices such as the Turbuhaler, but less so for the Diskus in which unit doses are sealed until priming (blistering).

In a previous study by Melani et al., it was found that patients exhale into a DPIs mouthpiece in up to 22% of cases. Being able to detect these exhalations through the use of an algorithm will allow clinicians to investigate if patients are using their DPIs correctly. The severity of the exhalation is important. If the drug has been released into the mouthpiece of a DPI, the power of the exhalation required to disperse the drug needs to be quantified. Knowing how powerful an exhalation needs to be before it adversely disperses the drug from the mouthpiece allows an effective threshold to be set in detecting such events through the use of an algorithm.

One aspect of the invention is to know the relationship between the intensity of an exhalation into the mouthpiece of a DPI and the amount of drug dispersed.

A Seretide Diskus DPI inhaler was used for experimental purposes. Blow-ins were classified as being either hard or soft in nature. The following simple procedure was performed for this experiment:

1. The inhaler was firstly weighed before being placed directly in front of the mouth of the subject.
2. The subject then proceeded to exhale or blow directly into the mouthpiece.
3. The inhaler was subsequently weighed once more to see the amount of drug that was dispersed.
4. Each time the inhaler was used the device recorded the acoustics of the blow-in.
5. Steps 1 to 3 were repeated for both the hard and soft blow-ins.

Figure 3:
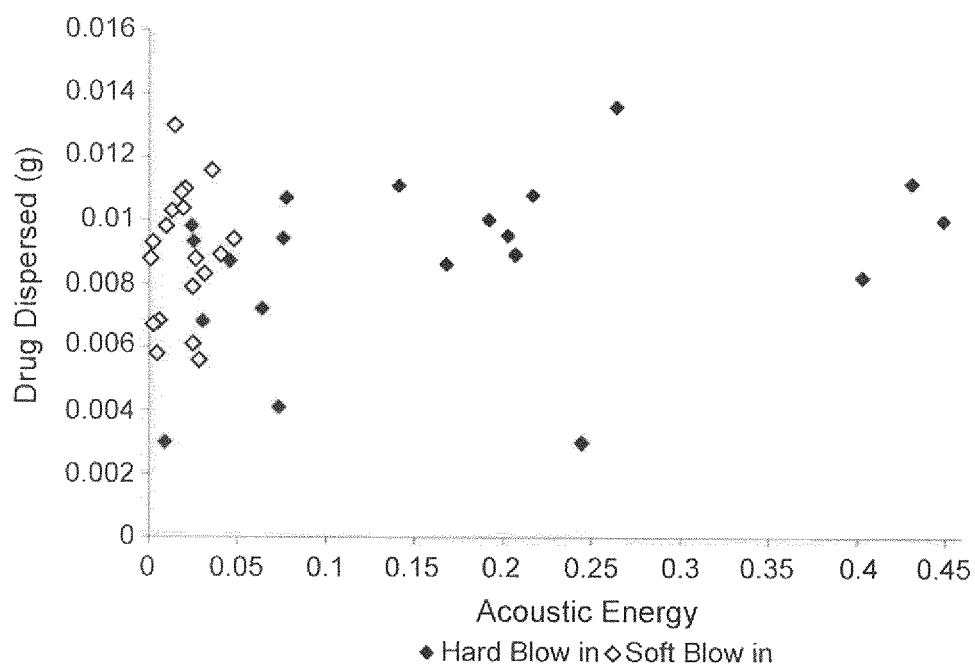
FIG. 3 illustrates the relationship between acoustic energy and amount of dug dispersed as a result of the blow-in using the "old" version of the device.
Figure 4:
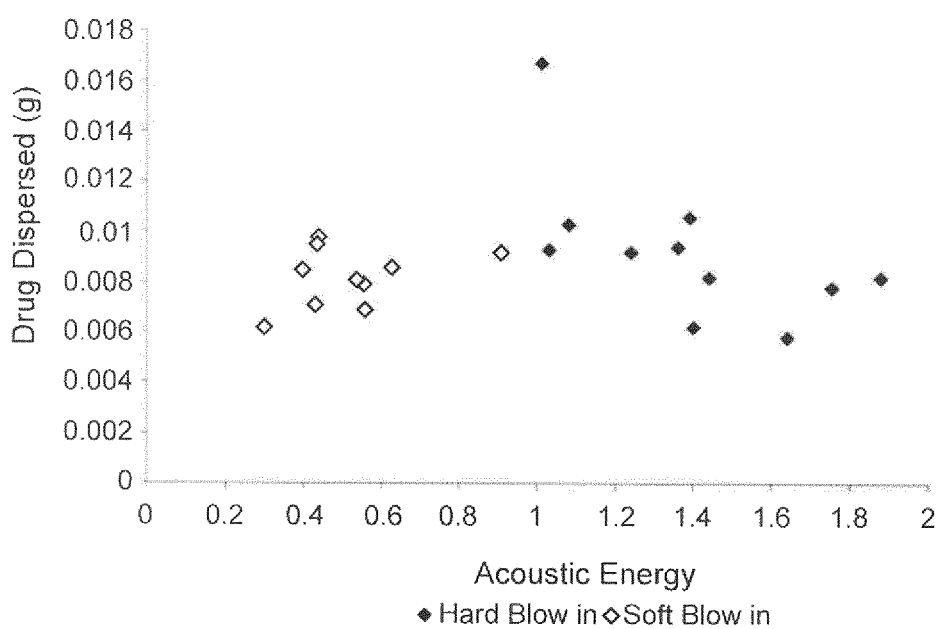
FIG. 4 illustrates the relationship between acoustic energy and amount of drug dispersed as a result of the blow-in using the "new" version of the device.

The FIGS. 3 and 4 illustrate the relationship between the acoustic energy and the amount of drug dispersed from the Diskus DPI. Exhalations or blow-ins were classified as being of a hard or soft nature. Hard blow-ins were exhalations until the residual volume while soft blow-ins were exhalations until functional residual capacity.

The Diskus DPI's used in this experiment contained the drug Seretide. This contained 50 mcg of salmeterol and 500 mcg of fluticasone propionate per dose, in addition to 12.5 mg of lactose (carrier) in each dose. Overall this equated to 13.05 mg of powder per dose. Other variations of Seretide may be used that contain a reduced amount of fluticasone propionate (250 mcg or 100 mcg).

After each individual blow-in the Diskus DPI was weighed on a weighing scale in order to calculate the amount of the Seretide drug dispersed. The acoustic energy was calculated using an algorithm designed to detect exhalations. The algorithm searches for energy bands between 20 Hz to 200 Hz. The acoustic energy is calculated for each section by multiplying the square of the median amplitude for each exhalation by its duration in seconds. The relationship between the acoustic energy and the drug dispersed is plotted on FIG. 3 and FIG. 4 respectively.

FIG. 3 contains data obtained from using the "old" device while FIG. 4 contains data from the "new" device. Two different versions of the device were tested to investigate if the findings of this experiment would differ.

From examining FIG. 3 it can be seen that there is a clear difference in the acoustic energy between the hard blow-ins and the soft blow-ins, as expected. However, in terms of the amount of drug dispersed there was no significant difference between the hard blow-ins and soft blow-ins. The same results are seen in FIG. 4.

It will be appreciated that the energy of a blow-in has the possibility to affect the amount of drug dispersed. However from this experiment it is clear to see that regardless of the intensity of the blow-in, the Seretide drug will be dispersed from the mouthpiece of the Diskus.

There are some instances in which the drug dispersed weighs more that the quantity of drug available in the blister (13.05 mg). Reasons for this may lie in the fact that for each blow-in, a small quantity of the drug will remain in the mouthpiece. Humidity introduced from the exhalation has the potential to cause the powder to clump together and attach to the side of the mouthpiece. While one blow-in might not dislodge this powder, a second blow-in may do so thus explaining the unnaturally high dispersion of drug.

Another observation to be noted is that the acoustic energy of the blow-ins is significantly higher in the new device compared to the old device. This may be due to the fact that the orientation of the microphone was changed from face up to face down.

The following conclusions can be deduced from this experiment:

Acoustic energy differs between hard and soft blow-ins for the Seretide Diskus DPI used in this experiment.

The type of blow-in does not affect the amount of drug dispersed, as a relatively soft blow-in has to potential to disperse just as much of the drug as a hard blow-in.

The only real way to prevent drug escaping the mouthpiece is to not blow directly into the mouthpiece.

Blow-ins are unfavourable events and a robust algorithm that can detect them, regardless of how powerful they are, is required. The question remains whether a blow-in that takes place in the vicinity of a device is classified as detrimental, even if no drug is dispersed. Further testing is required to investigate this.

Experiment 2

Figure 5:
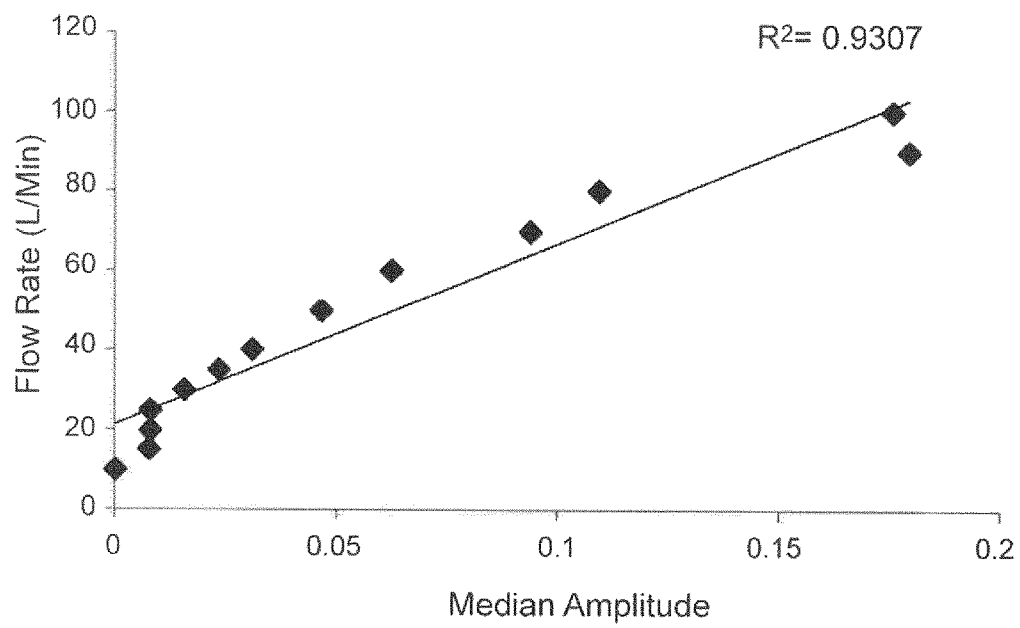
FIG. 5 illustrates the relationship between acoustic energy and flow rate for inhalations.
Figure 6:
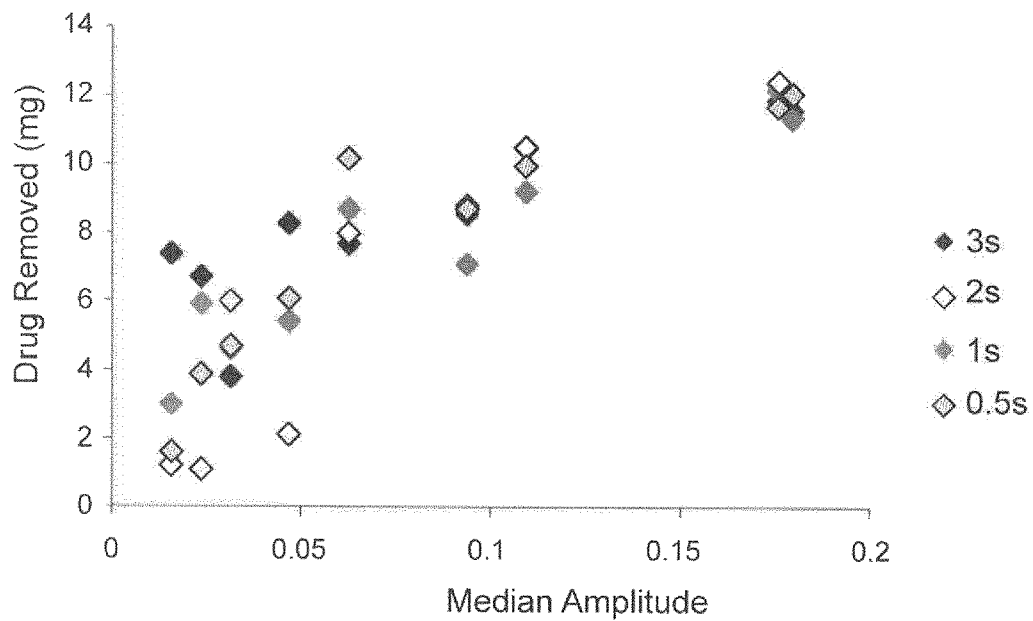
FIG. 6 illustrates the relationship between acoustic energy and amount of drug extracted from the inhaler as a result of inhalations.

This experiment is concerned with obtaining information in relation to the inspiratory flow rate/acoustic energy required to remove drug from the DPI during inhalations. This relationship is important in order to understand how effectively patients use their inhalers. Previous studies have indicated that in order for inhaler medication to be clinically effective it must have a minimum flow rate of 30 L/Min. While these studies have primarily focused on the effectiveness of drugs at varying flow rates, this experiment will simply aim to find out what acoustic energies remove what amount of drug from the inhaler. FIG. 5 illustrates the relationship between acoustic energy and flow rate for inhalations. FIG. 6 illustrates the relationship between acoustic energy and amount of drug extracted from the inhaler as a result of inhalations.

Although being able to accurately identify inhalations is an important step in adherence monitoring, being able to extract additional pertinent information from each inhalation and inform the Clinician on the effectiveness of each inhalation is a far greater step.

This experiment will seek to investigate and validate such relationships by looking at flow rates, the associated acoustic features and mass of drug removed from a Diskus DPI.

Figure 7:
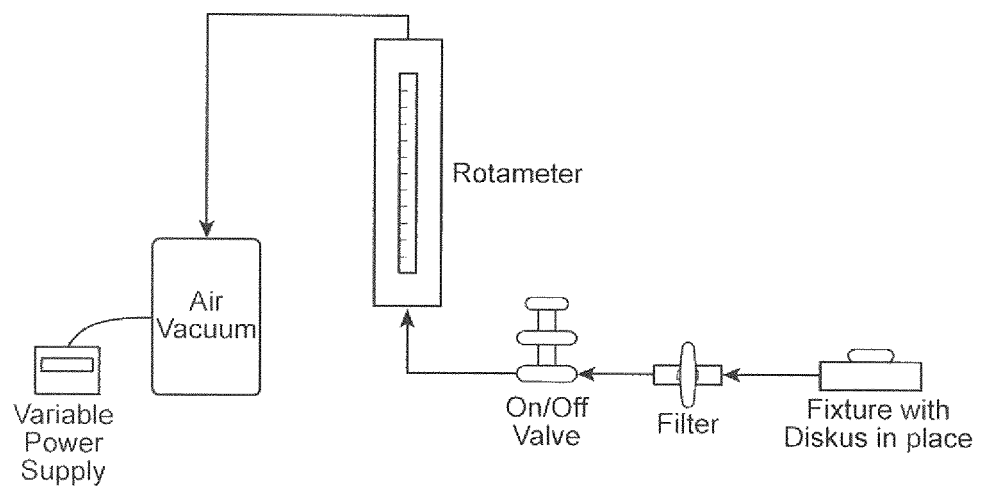
FIG. 7 illustrates an experimental setup for examination of relationship between inhalation energy and drug released from inhaler.

This experiment involved using an air vacuum to remove the drug from the Diskus inhaler. A Rotameter was used to measure the flow rate of the vacuum in liters per minute. A specially designed jig/fixture was used to hold the Diskus inhaler in place, as shown in FIG. 7.

The experiment was designed to ideally create a realistic flow at a required level. However merely connecting the apparatus, whilst turned on, to the inhaler would give uncertain results. This is because the vacuum flow would drop vastly from a high flow rate once connected to the DPI due to a change in resistance. A simple on/off valve was used to turn on the vacuum and suck the powder from the mouthpiece of the inhaler. This simulated the ramp of an inhalation as flow would begin at a low rate (0 L/min) and increase to a peak flow rate. The following sections will give details of the experimental protocol followed and the results obtained in addition to a discussion and conclusion of the experimental results. FIG. 7 illustrates the equipment set up required to carry out these experiments. The protocol for this experiment was:

A dummy Diskus was used to set the flow rate required. When the flow rate needed was reached the on/off valve was closed and the dummy Diskus was replaced with the test Diskus.

The test Diskus was weighed before being blistered and subsequently placed into the fixture to hold it securely in place. The on/off valve was opened for a set period of time depending on the inhalation duration required. The times used in this experiment were 0.5 s, 1 s, 2 s and 3 s respectively.

The test Diskus was removed after each test and weighed, measuring the mass of the drug removed during the simulated inhalation.

The test Diskus was cleaned out either after every single trial or every four trials, depending on the test being carried out.

The flow rates were adjusted by using the dummy Diskus and results obtained for the different inhalation times for flow rates ranging from 10 L/Min up to 100 L/Min.

In relation to flow rate vs. drug removed, it can be seen that the amount of drug removed from the inhaler reduces dramatically under 30 L/min. This finding is in agreement with previous literature that suggests that 30 L/Min is the minimum flow rate for an inhalation to be clinically effective. For this test the inhaler was only cleaned out every four runs, so as to mimic the actual use of the inhaler by a patient.

For the next test the inhaler was cleaned out after every run, it can be observed that even at flow rates above 30 L/Min the full weight of the drug is not being removed. This may have implications for the clinical efficacy of the inhalers, as the required dosage is not being reached.

The acoustic amplitude has an approximate linear relationship with flow rate. Also the acoustic energy has power relationship with flow rate. These findings can contribute to extracting pertinent information regarding inhalations. If an algorithm was used to detect inhalations from asthma patients using inhalers, then investigating the amplitude and energy of the inhalations would provide Clinicians with information regarding the effectiveness of each inhalation in relation to the amount of drug removed from the inhaler.

FIG. 6 shows the data from the DPI being aired out after every 4 tests. The tests were done from 3 seconds down to 0.5 seconds and then the DPI was cleaned out. The importance of duration at low acoustic energy values is particularly obvious here. An interesting result is that the increase in drug mass removed for test durations does not always occur. One can see from FIG. 6 that the tests done for 1 second removed more drug than the test carried out for 2 seconds in 5 cases. This shows that a user can take in more drug in some doses than others. This finding suggests that it may lead to surplus amounts of drug being delivered unintentionally as it may be stuck in the inhaler but added to a new dose giving a larger dose than required.

It will be appreciated that duration is an important factor in determining the amount of drug extracted from the inhaler during inhalations. The ability to ascertain the amount of drug released from the inhaler by combining measures of duration and acoustic amplitude will increase the system's power in assessing the quality of breath phases during inhaler use, i.e. improving technique error identification. This experiment provides with minimum acoustic thresholds from which to assess inhalation quality.

Experiment 3

Figure 8:
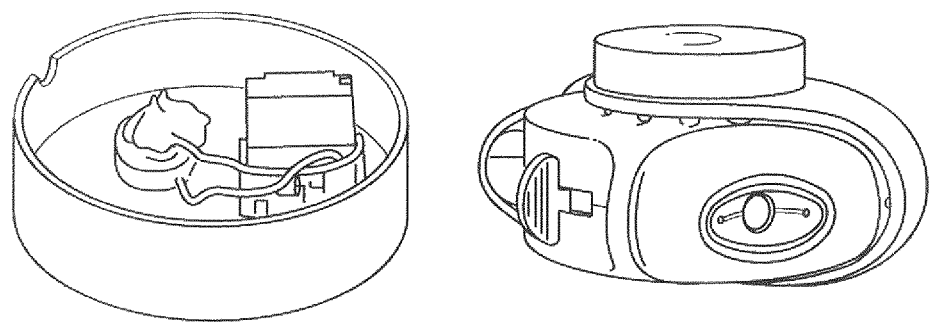
FIG. 8 illustrates on the left an adherence monitoring device and on the right an adherence monitoring device bonded onto the side of a Seretide Accuhaler/Diskus inhaler according to one embodiment.

20 asthma patients (11 female & 9 male) who attend an outpatient's respiratory clinic were recruited for this study. The age range was 20-68 (mean 43.5±standard deviation 14.2). Subjects had all previously been prescribed Seretide inhalers and were very familiar with the mechanics of using such inhalers. Subjects were each given a Seretide Accuhaler/Diskus type inhaler with the adherence monitoring device attached and instructed to use the dry powder inhaler as one normally would in a clinical visit. FIG. 8 illustrates on the left an adherence monitoring device and on the right an adherence monitoring device bonded onto the side of a Seretide Accuhaler/Diskus inhaler according to one embodiment. The addition of the adherence monitoring device did not impact on the normal functioning of the inhaler. Each time the inhaler is opened the adherence device switches on and records the acoustic signal until the inhaler is subsequently closed. The subject's inhaler use was recorded for a period of three months, with each subject returning to the clinic at monthly intervals to have their inhaler recordings uploaded to a database.

Adherence Monitoring Device

This study uses the Seretide Accuhaler/"Diskus" inhaler in conjunction with an attached adherence monitoring device (Manufactured by Vitalograph (Ireland) Limited). The adherence device consists of a microphone, a microcontroller, a battery and a micro SD card. The microphone is a medium quality Knowles Acoustics SPM0204HE5 microphone. The adherence device was bonded securely to one side of the Diskus inhaler, as can be seen in FIG. 8, allowing patient use of the inhaler to be seamlessly recorded.

The adherence device is activated, i.e. begins recording, the first time the diskus inhaler is opened. Each time the inhaler is used by a patient an audio file of the event is recorded and saved as a mono way file, sampled at 7913 samples/second with a bit depth of 8 bits/sample, on the memory card. The adherence device goes into sleep mode, to conserve power, when the inhaler is closed.

Figure 9:
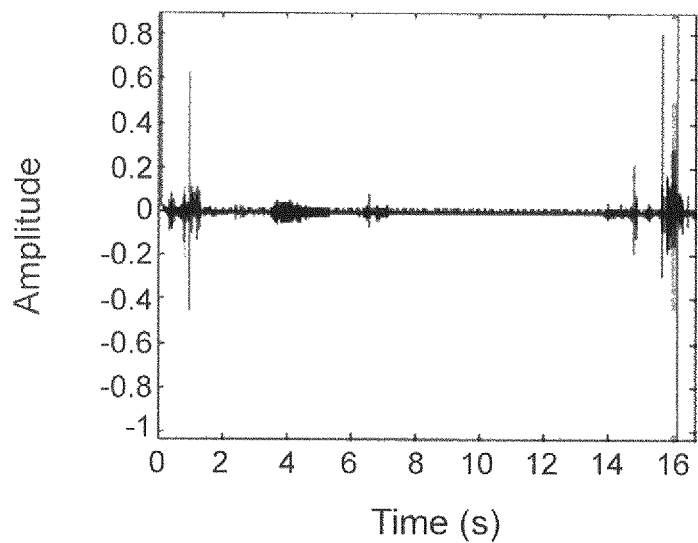
FIG. 9 illustrates an acoustic signal from a typical inhaler recording with an inhalation present between time 3.5 to 5.5 s.

The acoustic signal of a typical patient recording is shown in FIG. 9. The correct procedure for using the Seretide Diskus inhaler involves firstly sliding the device open to reveal the mouthpiece (t=0 s), sliding a lever that releases a dose of medication into the mouthpiece (t=1 s), taking an inhalation (t=3.5-5.5 s), holding ones breath for about 10 seconds (t=5.5-15 s) and finally sliding the device closed.

Signal Processing

The algorithm employed to identify and detect the temporal onset/offset of inhalations can be broken up into two distinct sections. The first section involves identifying and demarcating inhalation type events in the recordings, while the second stage involves removing false positives i.e. false inhalation classifications.

Extracting mel frequency cepstral coefficients (MFCCs) is a parameterization method for vocalization, due to the fact that MFCCs model the known variation of the human ears critical bandwidth with frequency. It is known that breath sounds have a characteristic pattern which allows them to be distinguished from other sounds. Based on this observation an algorithm was designed to detect this pattern.

The algorithm firstly went through a training procedure on a set of 20 randomly selected inhaler recordings. Each signal was separated into frames of length 700 ms which overlapped every 20 ms. 12 MFCCs were calculated for each frame in the signal, forming a short-time cepstrogram of the signal. Using Singular Value Decomposition (SVD), a normalized singular vector was computed from the cepstrogram of the signal. Singular vectors can be used to capture the most important characteristics of breath sounds obtained from MFCC calculations. An adaptive threshold is automatically set that is 14% higher than the lowest singular vector in the inhaler recording. Singular vectors above the adaptive threshold were marked as potential inhalation events, while those below it were discarded. This adaptive threshold was found empirically to produce the most accurate detection of events, and subsequently inhalations in the training set.

In the second stage of the algorithm, the zero crossing rate (ZCR) and median amplitude were computed to reduce the number of false positives detected by the algorithm, i.e. artefacts classified as inhalations. Inhalations were empirically found to have a characteristically high ZCR compared to that of non-inhalations in the training set. A fixed threshold constant of 0.17 was therefore introduced to reflect this fact. In the training set, inhalations consistently had a ZCR above this threshold value, while false positives were successfully removed.

$$ZCR = \frac{1}{N}\sum_{n=N_0+1}^{N_0+N-1} \frac{1}{2}|\text{sign}(x[n]) - \text{sign}(x[n-1])| \qquad (1)$$

The median amplitude of the proposed inhalation event was also calculated. Similar to the ZCR threshold, a fixed threshold was introduced to remove false positives based on empirical observations from the training set. Inhalations were found to have a median amplitude threshold value higher than 0.012, while any artefact lower than this threshold was discarded. This combination of threshold values was empirically found to produce the most accurate detection of inhalations in the training set, and was thus applied to a new validation set of 255 separate files.

Results

Figure 10:
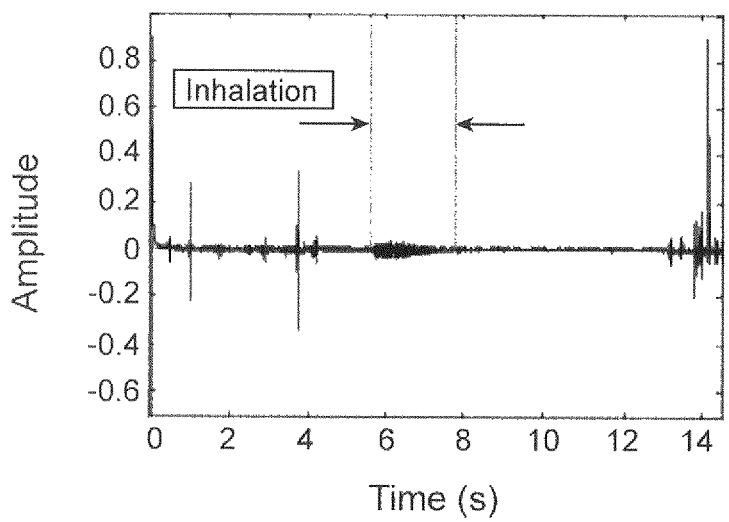
FIG. 10 illustrates the identification and temporal onset/offset detection of an inhalation (indicated by the arrows) in a typical inhaler recording by the algorithm.

The algorithm was applied to acoustic signals obtained from asthmatic outpatients who attended a respiratory clinic. FIG. 10 shows the identification and temporal onset/offset detection of an inhalation in a typical inhaler recording. The algorithm was designed so that various artefacts such as speech, fumbling of the inhaler and background noise are not detected as events. Both the onset and offset time of the inhalation are calculated by the algorithm.

In order to validate the algorithm, 255 audio files were selected at random to be analyzed from the inhaler recordings database. The audio files were randomly selected from 12 out of 20 subjects who were part of the study and the files were also selected at random from the three months of recordings from each subject. Two human raters, trained by an experienced Respiratory Clinician on how to identify inhalations, independently classified each of the 255 audio files by visual and aural inspection. The human raters firstly identified if an inhalation was present and secondly demarcated the onset and offset time of the inhalation. The human raters agreed on the presence of inhalations in 100% of the audio files. The average difference between raters in the detection of the inhalations onset time was ±19 ms, while the average difference in the offset times was ±15 ms.

Table I shows the performance of the algorithm in detecting inhalations, compared to that of the human raters. Results were classified as True Positive (TP), False Positive (FP) and False Negative (FN), according to the classification of the human raters. It was found that the algorithm had sensitivity (Sen) of 95%, specificity (Spe) of 94% and accuracy (Acc) of 89% in detecting inhalations.

TABLE I

PERFORMANCE OF TABLE OF THE ALGORITHM

| Inhaler Recordings | Total # Inhalations | TP | FP | FN | Sen | Spe | Acc |
|---|---|---|---|---|---|---|---|
| 255 | 255 | 242 | 16 | 13 | 95% | 94% | 89% |

The result of the algorithm in accurately identifying the onset and offset of the inhalations is shown in Table II and Table III respectively. For this analysis only the true positive inhalations were considered. For inhalation onset time, the average difference between the human raters was ±57 ms and ±61 ms respectively. For inhalation offset time, the average difference was ±104 ms and ±107 ms. Taking into consideration that an average inhalation was found to be 1.8 s in duration, the algorithms inhalation onset time classification varied by ±3.16-3.38%, compared to that of the human raters classification. Furthermore the algorithms inhalation offset time was found to vary by ±5.77-5.94%, compared to that of the human raters" classification.

TABLE II

INHALATION ONSET TIME ACCURACY

| | Inhalation Onset Time | |
|---|---|---|
| | Rater 1 V. Algorithm | Rater 2 V. Algorithm |
| Average Difference (+/−) | 57 ms | 61 ms |

TABLE III

INHALATION OFFSET TIME ACCURACY

| | Inhalation Offset Time | |
|---|---|---|
| | Rater 1 V. Algorithm | Rater 2 V. Algorithm |
| Average Difference (+/−) | 104 ms | 107 ms |

The system of the invention has been designed to automatically detect and demarcate inhalations from recordings of inhaler use in real world environments. Validation of the algorithm was completed by running it on 255 audio files obtained from asthma patients actual inhaler recordings and comparing it to results from manual classification. Results have indicated that the algorithm was able to detect, on average, inhalations in 95% of audio recordings that contained inhalations according to the human raters. The algorithm had a specificity of 94%, while accurate identification of inhalations took place, on average, in 89% of audio files. This high level of accuracy is a promising result if this approach is to be included in a fully automated system for identifying inhalations from audio recordings.

Of the inhalations that the algorithm detected, it was observed that it was able to identify the onset/offset times of inhalations with a high degree of accuracy.

In comparison to the human raters, the algorithm differed in inhalation onset time by ±57 ms and ±61 ms and in inhalation offset time by ±104 ms and ±107 ms. A possible explanation as to why the algorithm was not as accurate in detecting the inhalation offset time, compared to that of the onset time can be found in the mechanics of inhaler use.

Inhalation of asthma medications using inhalers involves a deep and steady inhalation from the user, in order to inhale the drug successfully into the small airways of the lungs. Such inhalations have a characteristic pattern, in both the time and frequency domains, when the correct inhalation technique is followed by the users. The onset of an inhalation is commonly accompanied by a period of silence in the period before the inhalation takes place. Although artefacts can occasionally interfere with the accuracy of the inhalation onset time identification, the algorithm achieves good correlation compared to that of the human raters.

The accurate identification of the offset time of inhalations from inhaler recordings represents a more challenging task. As patients inhale the drug from their inhalers there is a tendency to gradually reduce inhalation flow rate in the last few hundred milliseconds of the inhalation. At the end of the inhalation the patient will remove their lips from the mouthpiece of the inhaler device before clasping their mouth shut and holding their breath. The reduction in the flow rate of the inhalation towards its completion, the sound artefacts produced by the removal of the lips from the mouthpiece, in addition to artefacts associated with the fumbling of the inhaler as it is removed from the area of the mouth, are a number of factors which contribute to making the accurate identification of inhalation offset times challenging.

In one version of the algorithm may comprise the following modifications:
  Bandpass filtering of the audio above 1300 Hz
  Comparing the mean amplitude of identified inhalations to thresholds calculated from experiment 2 will generate a classification of the quality of the inhalation identified
  Measuring Peak inspiratory flow (PIF) rate from the acoustic signal to provide an objective measure of lung health from inhalers.

It will be appreciated that the invention provides an algorithm that can accurately detect and demarcate inhaler recordings has a wide range of implications for both clinicians and asthma sufferers. Incorporating this algorithm into devices that can record audio signals of patients taking their asthma medication opens the door to a completely new approach to adherence monitoring. The algorithm provides a fast and easy method to analyze patients' inhaler use and thus can provide clinicians with strong empirical evidence of patients' adherence to their medication. This information can be used to give active feedback to patients. Such feedback may encourage patients to take better control over their asthma and lead to an overall improvement in their adherence to their medication. This in turn may improve the efficacy of the drug treatment regime, reduce the occurrence of asthma attacks and decrease hospitalizations.

It will be appreciated that applications of the algorithm include extracting pertinent features from inhalations which may be used to provide real time information on patient's lung conditions in a remote monitoring scenario.

In one embodiment the algorithm is adapted to automatically analyse patient inhaler adherence. A patient's temporal adherence to their inhaler medication can be analysed from the time and date stamp of each audio file obtained. Technique adherence can be analysed through the detection of the breath and blister events in the audio signal, the number of each event present and the order in which the events take place. The invention provides a means for all of this information on inhaler use to be compiled into an easy to understand and accessible format for both the clinician and patient.

Acoustic Recording Device

As described above the device according to one embodiment of the present invention can be used in conjunction with a commonly used Diskus inhaler. The device starts recording once the Diskus inhaler is opened and switches off when the Diskus is closed. The acoustics of inhaler use are recorded as mono WAV files, at a sampling rate of 8000 Hz and resolution of 8 bits/sample. The device has sufficient battery life to record patient inhaler use for up to a period of one month.

To validate the performance of an algorithm data was recorded from 12 community dwelling asthmatic patients (6 female & 6 male). The age range of patients recruited was 20-83 (mean 49±18 years old). All patients had previous experience of using the Diskus DPI. The Diskus used contained the combination drug Seretide which is comprised of both salmeterol and fluticasone propionate. In each inhaler there were 60 doses of Seretide drug.

Each patient was given a Diskus inhaler by their clinician attached with the device for a period of one month. The device was bonded securely to the side of the inhaler, from where it did not impact on the mechanics of inhaler use. Patients were instructed to use their inhaler as normal and they were not given any extra advice or special training. Patients used their inhaler as part of their normal daily routine. After using their device enabled inhaler for one month the patients returned to their clinic from where the device was removed from the inhaler and the audio files were uploaded to a database for analysis.

Correct Diskus Inhaler Use

The Diskus inhaler was originally designed to facilitate easy use and patient acceptability and is illustrated in FIG. 1. When patients are given a Diskus inhaler they are instructed on how to use the device correctly by their clinician. To validate the device of the present invention patients were instructed to use their inhaler twice daily. As there were 60 doses in each inhaler, this corresponds with 30 days of correct usage. The Diskus is opened by sliding a thumbgrip to expose the mouthpiece. When this occurs the device switches on and begins to record audio. A lever is then pulled back which opens a blister foil containing medication inside in the mouthpiece (blister event). A click noise indicates that the blister foil was pierced and that there is medication available in the mouthpiece for inhalation. The patient is then instructed to exhale gently away from the mouthpiece, taking particular care not to exhale into the mouthpiece. They should then seal their lips tightly around the mouthpiece, inhale steadily and deeply and hold their breath for 10 seconds. The patient should then exhale slowly after the 10 seconds. Once this is complete the patient should use the thumbgrip again to slide the Diskus back to its original position. When the Diskus is fully closed the device will switch off and save the audio file to its internal memory storage.

Technique Adherence Algorithm

Figure 11:
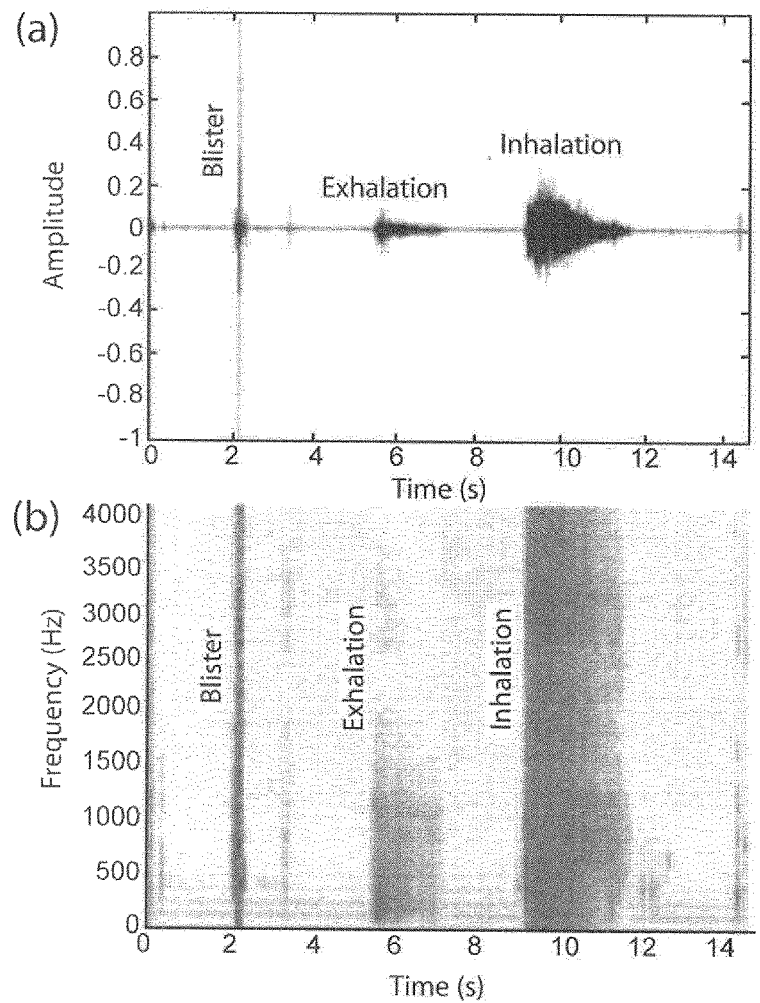
FIG. 11 shows the presence of blister, exhalation and inhalation events in (a) time domain and (b) spectrogram of signal illustrating ideal use of an inhaler.
Figure 12:
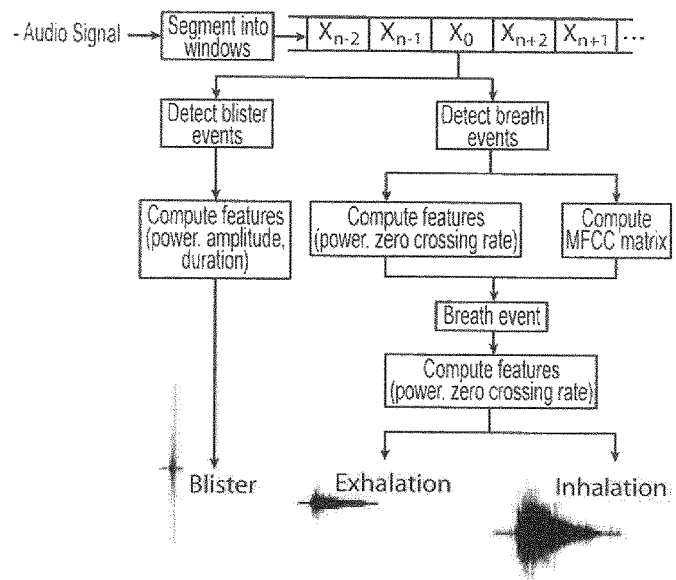
FIG. 12 illustrates a block diagram of the basic steps of the algorithm takes to analyze inhaler recordings according to one embodiment of the invention.

The algorithm designed to detect the common inhaler events initially went through a training phase. The 12 patients recruited provided 609 audio files in total. Of these, 202 (33% of total files available) were randomly selected and employed in the training phase of the algorithm. This specific quantity of files were selected for the training phase in order to develop a robust estimate of typical inhaler use. The inhaler events to be detected specifically from the audio recordings are blisters and breaths (both inhalations and exhalations). To detect the blister events, features such as the mean power at select frequency bands, amplitude and duration are computed. The presence of blister, exhalation and inhalation events are shown in FIG. 11 (a) time domain and (b) spectrogram of signal illustrating ideal use of the inhaler. A mel frequency cepstral coefficient (MFCC) approach was employed to detect breaths in this study, due to the fact that breaths have a characteristic MFCC pattern that allows them to be distinguished from other sounds. A block diagram of the basic steps the algorithm takes to analyze inhaler recordings is shown in FIG. 12.

As previously mentioned the algorithm computes the MFCCs to detect breaths in this study. Extracting MFCCs is a parameterization method for vocalization, due to the fact that MFCCs model the known variation of the human ears critical bandwidth with frequency. It will be appreciated that other methods exist which can be used to detect breaths, such as support vector machines (SVM) and Gaussian mixture models (GMM) can be used.

The algorithm automatically examines each audio file in four distinct stages. The algorithm firstly identifies the piercing of the blister containing the drug (Stage 1), before identifying the breath sounds (Stage 2). It then differentiates each detected breath sound as either an inhalation or an exhalation (Stage 3). Lastly the algorithm calculates a score of user technique (Stage 4) for each individual audio file. This technique score is based on the presence of the blister and breath events in Stages 1-3, the order in which they take place and the quantity of each event.

Figure 13:
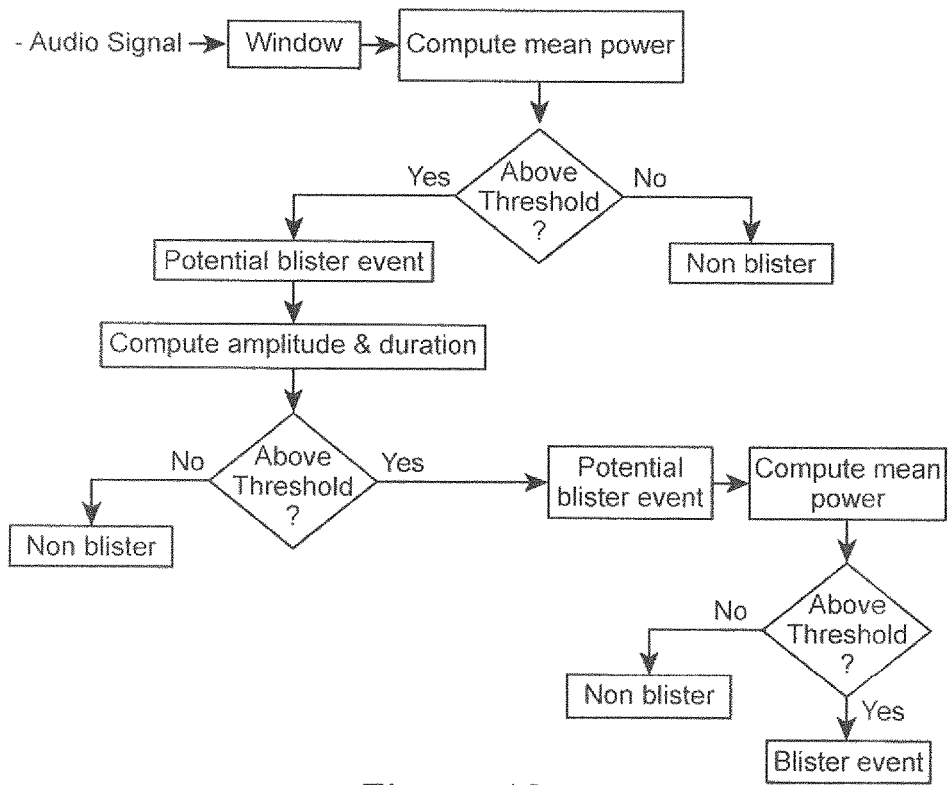
FIG. 13 illustrates a flow chart of the steps employed to detect blister events and how they can be displayed.

The first quantity of the algorithm involves detecting the piercing of the blister foil containing the medication. The audio signal is segmented into windows of length 100 ms, with an overlap of 10 ms. The mean power spectral density (PSD) is calculated for frequencies between 2000 Hz-3000 Hz. For this frequency band it was found from empirical observations in the dataset that blister sounds had a mean power greater than −65 dB. The reason the power in this frequency band was greater for blisters compared to non-blisters is due to the intrinsic sound associated with the blistering of the drug foil in the Diskus inhaler. A fixed threshold was set with any segments greater than this threshold considered as potential blister sounds. The algorithm then examines the proposed blister sounds to remove any false positives. Potential blister sounds with maximum normalized amplitude less than 0.7 are removed, in addition to potential blister sounds greater than one second in duration. Finally the mean PSD in the 20 Hz-200 Hz frequency band is calculated. It was found from the training dataset that blisters had a mean PSD greater than any false positives in this frequency range, due to the distinctive sound of a blister. Any potential blisters with a power less than −62 dB are considered as false positives and removed, thus leaving only the true positive blister events. A flow chart of the steps employed to detect blister events is displayed in FIG. 13.

Stage 2 of the algorithm involves detecting breath sounds. The audio signal is first filtered to remove high frequency components above 1400 Hz using a low-pass type I 6th order Chebyshev filter. Each signal is separated into frames of length 700 ms with an overlap of 20 ms. Twelve MFCCs are calculated for each frame, forming a short-time cepstrogram of the signal. Singular value decomposition (SVD) is then employed to obtain a normalized singular vector from the cepstrogram of the signal. Singular vectors capture the most important characteristics of breath sounds obtained from MFCC calculations. An adaptive threshold is set that is 7% higher than the lowest singular vector in the inhaler recording. Singular vectors above this adaptive threshold are marked as potential breath events, while those below it are discarded. This adaptive threshold was found empirically to produce the most accurate detection of breaths in the training set. The mean zero crossing rate (ZCR) is then computed to reduce the number of false positive breaths detected by the algorithm using Equation 1, mentioned above.

Breaths were found to have a characteristically high ZCR compared to that of non-breaths in the training dataset. A fixed threshold constant of 0.1 was therefore introduced to reflect this fact. In the training dataset, breaths consistently had a ZCR above this threshold value, while false positives were successfully removed.

Figure 14:
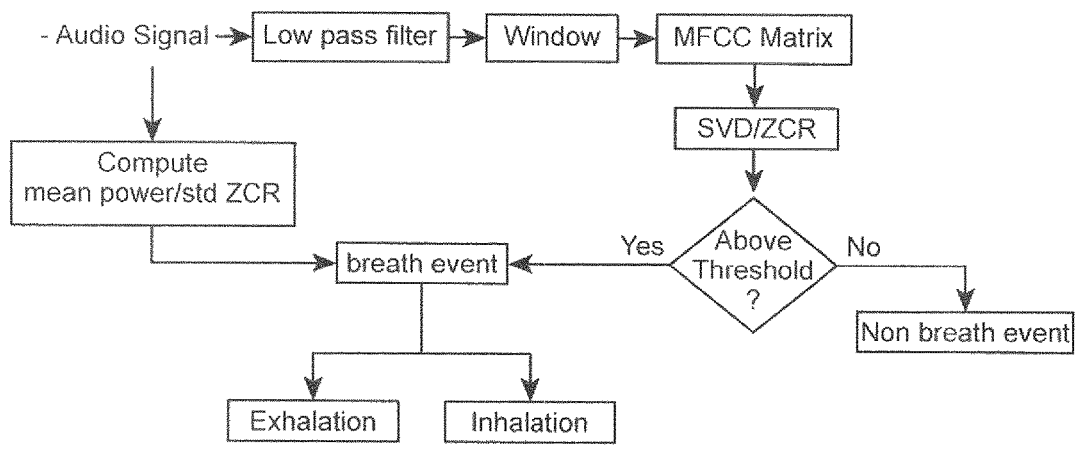
FIG. 14 illustrates a flow chart of the processing steps of the algorithm employed to detect inhalations and exhalations in the audio files.

Stage 3 involved differentiating breaths into inhalations and exhalations. To do this the mean power spectral density (PSD) of identified breaths is calculated for frequencies between 2520 Hz-4000 Hz in the original unfiltered signal. It was found from empirical observations in the training dataset that inhalations had a greater power in this specific frequency band compared to exhalations. Based on this fact a fixed threshold can be put in place. Inhalations were found to have a mean power greater than −80 dB and exhalations were found to have a mean power below this value. The standard deviation of the ZCR was also found to be higher for inhalations in comparison to exhalations in the training dataset. A fixed threshold of 0.045 was put in place with inhalations having a value greater than this threshold and exhalations a value below this threshold. A flow chart of the processing steps the algorithm employed to detect inhalations and exhalations in the audio files is displayed in FIG. 14.

Figure 15:
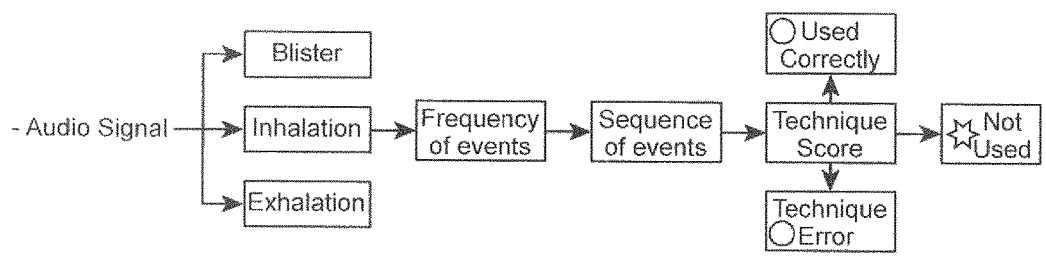
FIG. 15 illustrates how the algorithm checks to see what events have taken place, the frequency of any such events and the order in which these events have taken place.

The last stage of the algorithm (Stage 4) is to analyze all of the events which took place in the audio file and make a decision regarding the quality of a patient's inhaler technique. This information is outputted as a score which can be one of three possibilities; (1) used correctly, (2) technique error or (3) not used. To come to this decision the algorithm checks to see what events have taken place, the frequency of any such events and the order in which these events have taken place, as shown in FIG. 15.

The inhaler is deemed to have been used correctly if a patient first blisters the foil and secondly inhales the medication. For the purpose of this algorithm it was decided that an exhalation event does not need to be present in order for the inhaler to have been used correctly. Exhalations can take place before the blister or after the inhalation, still leading to a 'used correctly' score from the algorithm. However, if the patient exhales forcefully in the time between the blister and inhalation then they are judged to have committed a 'technique error' as they may have exhaled into the mouthpiece of the inhaler and dispersed some of the medication. Such a scenario is viewed as a critical error. Any other sequence of events is deemed to be a technique error. For example: An inhalation followed by a blister, a blister but no inhalation, inhalation but no inhalation etc. If the algorithm detects two or more inhalations or blisters then a technique error will also be judged to have taken place.

To test the algorithm's performance 407 new audio files were selected from the 12 asthmatic patients recruited (67% of total audio files obtained). Two human rates, trained by an experienced respiratory clinician to identify correct/incorrect Diskus inhaler use, independently classified each of the 407 audio files using the audio tool Audacity®. Each human rater manually examined the audio files using visual and aural methods and scored each individual audio file one of the three possible outcomes: (1) used correctly, (2) technique error or (3) not used.

Temporal Adherence Analysis

As previously mentioned the device also provides information regarding the exact time and date that the Diskus DPI was employed. Using this data the algorithm automatically computed the number of doses that were taken each day and represented this information in bar chart format. Any audio files less than one second in duration are discarded for this analysis due to the fact this is not a sufficient time period to use the inhaler adequately.

Figure 16:
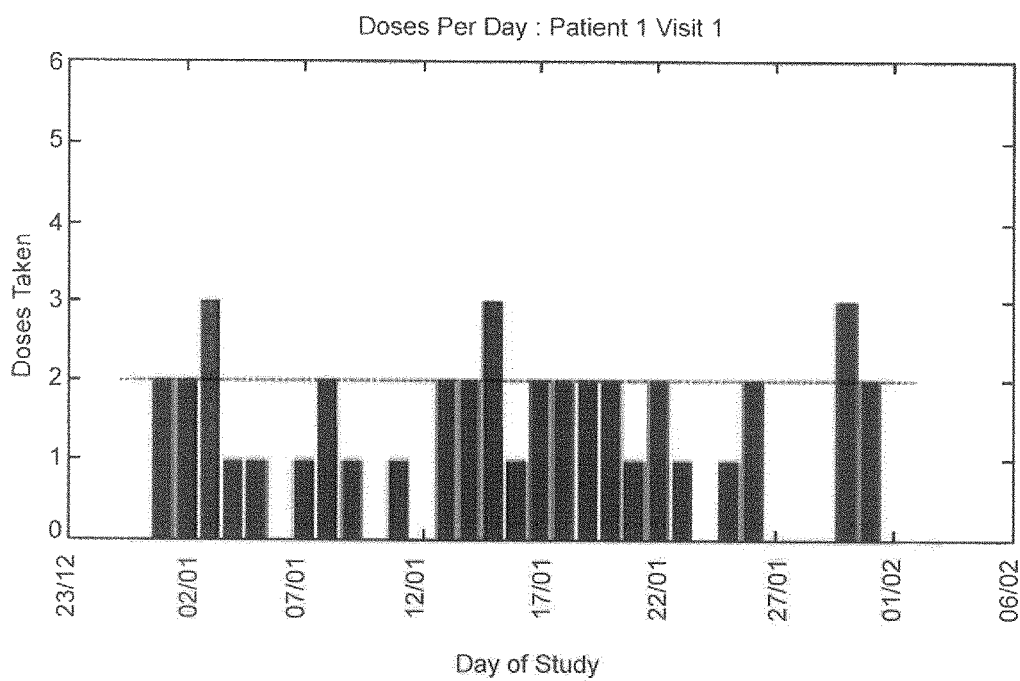
FIGS. 16 and 17 illustrates typical outputs from the algorithm that can be employed to evaluate or display a patients temporal adherence.

The algorithm designed is adapted to detect blister, inhalation and exhalation events, analyze the frequency of each event, in addition to the order they took place and output a score on user technique each time the inhaler was employed. The algorithm also analyzed the time and date the inhaler was operated in order to generate feedback on a patient's temporal adherence. FIG. 16 illustrates a typical output from the algorithm that can be employed to evaluate patient temporal adherence. In this bar chart graph one can observe if a patient overdoses, underdoses or takes the correct amount of doses of their medication for each single day that they should be using their inhaler.

Figure 17:
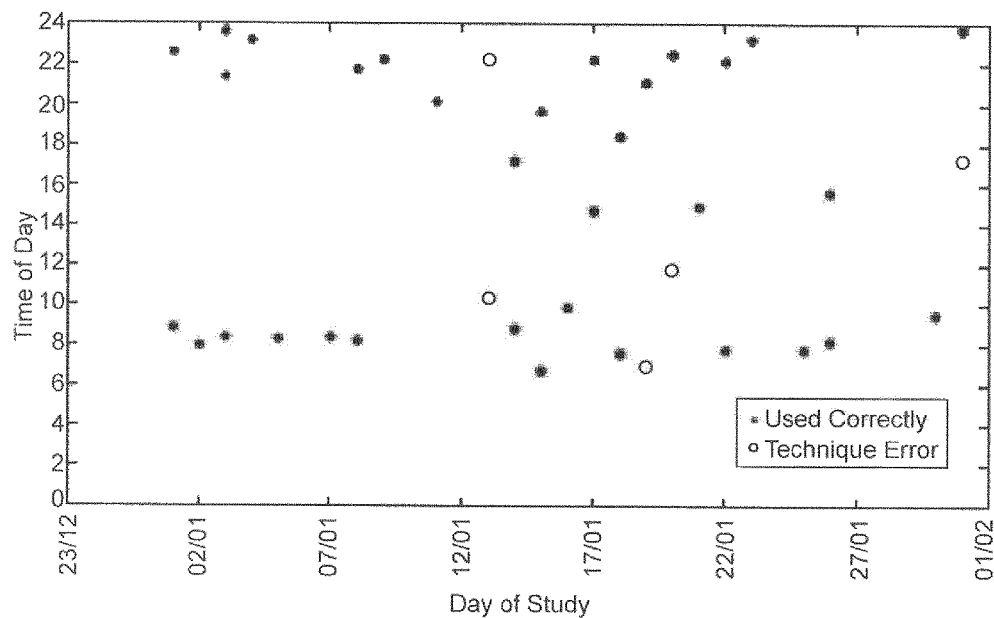
Figure 18:
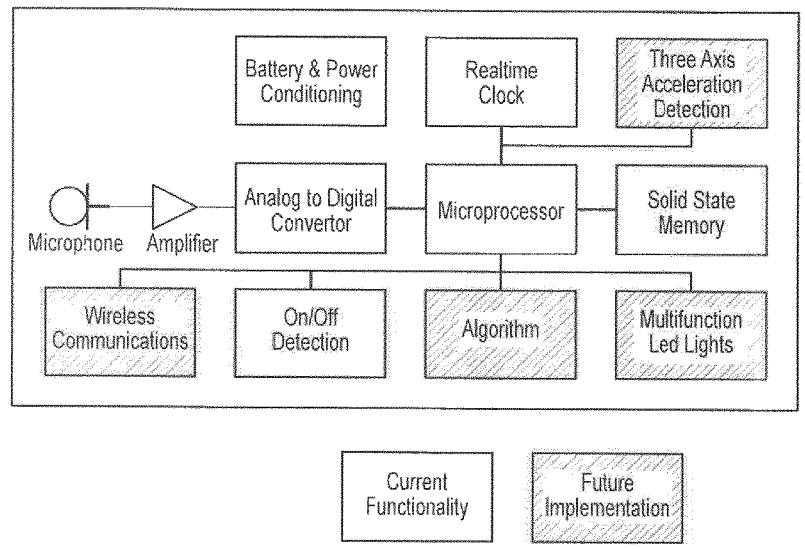
FIG. 18 illustrates a block diagram of the components to make up the inhaler device according to one embodiment of the invention.

The patient user technique score for each inhaler audio file, as computed by the algorithm, is stored in a text file. However, for the purposes of presenting the specific technique score the algorithm computes to both clinicians and patients, it was decided that a more interpretable version of presenting this information would be needed. Previous research has suggested that people perceive visual cues most accurately from information positioned along a common scale. Based on this information the best method of visualizing data is with the use of scatterplots and bar charts. It is for this reason that a bar chart graph was used to display information on temporal adherence. Colours are also widely used in data visualization to indicate appropriate levels of risk (i.e. green=safe, red=danger). A traffic light scatterplot was created to display the algorithms results on technique adherence. An example of such a graph is displayed in FIG. 17. This output graph displays information on the time and date the inhaler was used, in addition to how the inhaler was used. A colour green indicates that the inhaler was used correctly while the colour orange indicates that there was a technique error. This allows clinicians to examine a patient's adherence to their inhaler medication, while it also provides a method for patients to easily understand when and how they are using their inhaler. FIG. 18 illustrates a block diagram of the components to make up the inhaler device according to one embodiment of the invention as hereinbefore described.

Figure 19:
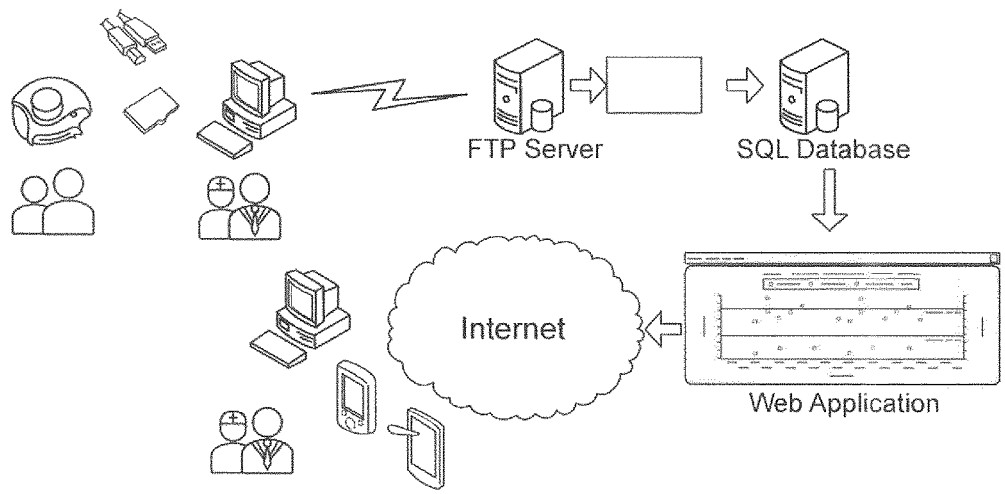
FIGS. 19 and 20 illustrate sample network architecture to facilitate implementation of the invention.
Figure 20:
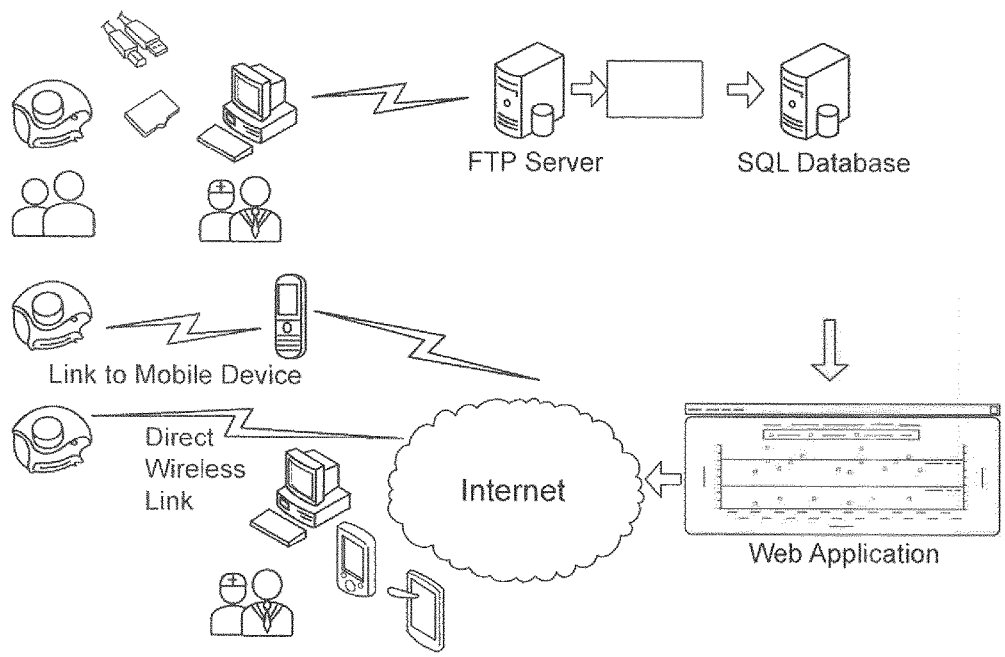

In another aspect of the invention the device of the invention can be used with a webportal service as shown in FIGS. 19 and 20. The webportal is an online system for collating, organising and visualisation the results of monitoring inhaler protocols. The webportal uses the audio recordings, their file names and the output of the processing algorithm as inputs to provide the user with detailed information about inhaler use.

Recordings extracted from the device are uploaded to the webportal server. The time and date of each recording is extracted from the timestamp of the audio recording, i.e. the file name and this information is used to present a visual representation of times at which the inhaler was used. The plotting of this data reflects inhaler events that are out of recommended inhaler usage i.e. doses of medication that are taken too early, indicating over dosing and doses of medication that are taken too late, indicating missed doses.

The webportal facilitates manual classification of audio recordings. The manual classification enables the user to listen to each recording and classify it according to a set number of options such as: pass, fail, "exhalation present after blister and before inhalations" and "breath not held for 5 seconds". These options have been set in accordance with research that has been carried out in terms of diskus inhalers but can be modified to include options that are appropriate for other inhalers. The output of the manual classification will be illustrated on the plot. The webportal can also read the output results of the processing algorithm and display the results in a visual format. The algorithm classifies each recording as Pass, Fail or Incomplete and the associated reasons for incomplete and fails, these are all illustrated in the generated plots. The webportal also provides an over reading function, all files can be checked by an over-reader and agreement or disagreement noted. The webportal can be adjusted to reflect various inhaler use protocols and additional errors that might be observed with different inhalers.

A typical use of the webportal in accordance with the invention is where a patient returns the device to a clinician who uploads the data to the Webportal. The algorithm processes the uploaded data and provides a plot of the latest inhaler events classified in terms of timing adherence and technique adherence. The clinician would be able to visually inspect the data to determine if the patient is using their inhaler correctly, both in terms of taking doses and inhaler technique and advise on any strategy to improve adherence. The clinician can also view adherence profiles for previous months to determine if there are any long term problems with adherence that may require additional intervention. It will be appreciated that part of the algorithm functionality can be stored on the inhaler device or a separate computer device. The data recorded by the inhaler device can be downloaded to the separate computer device for post-processing the data as hereinbefore described.

The embodiments in the invention described with reference to the drawings comprise a computer apparatus and/or processes performed in a computer apparatus. However, the invention also extends to computer programs, particularly computer programs stored on or in a carrier adapted to bring the invention into practice. The program may be in the form of source code, object code, or a code intermediate source and object code, such as in partially compiled form or in any other form suitable for use in the implementation of the method according to the invention. The carrier may comprise a storage medium such as ROM, e.g. CD ROM, or magnetic recording medium, e.g. a memory stick or hard disk. The carrier may be an electrical or optical signal which may be transmitted via an electrical or an optical cable or by radio or other means.

In the specification the terms "comprise, comprises, comprised and comprising" or any variation thereof and the terms include, includes, included and including" or any variation thereof are considered to be totally interchangeable and they should all be afforded the widest possible interpretation and vice versa.

The invention is not limited to the embodiments hereinbefore described but may be varied in both construction and detail.

What is claimed is:

1. A system for monitoring user technique of an inhaler device configured for delivery of a medicament, said system comprising:
   a first microphone configured to sense sound made during operation of the inhaler device;
   a second microphone adapted to determine inhalation or exhalation breath characteristics and/or cancel ambient noise; and
   processing circuitry operable to process a data signal obtained from the microphone, wherein said data signal comprises acoustic information sensed,
   wherein the processing circuitry is configured to determine inhalation and exhalation breath characteristics that occur during use, by analyzing the temporal and spectral components of the acoustic information sensed and processed to differentiate between an inhalation and an exhalation, based on both the temporal and spectral components.

2. The system of claim 1 wherein the processing circuitry further comprises a module for identifying drug priming or blistering characteristics of the device to identify that a medicament is about to be delivered before an inhalation.

3. The system of claim 1 wherein the processing circuitry further comprises a module for identifying drug priming or blistering characteristics of the device to identify that a medicament is about to be delivered before an inhalation and the drug priming characteristics comprises an acoustic signal generated by a mechanism for priming the medicament configured to release the medicament that generates a unique energy profile of the activation mechanism convolved with the noise of release the medicament.

4. The system of claim 1 wherein analysis of the temporal and acoustic components provide an indicator of temporal adherence indicating correct volume of medication is delivered at correct temporal intervals.

5. The system of claim 1 wherein analysis of the temporal and acoustic components provide an indicator of temporal adherence indicating correct volume of medication is delivered at correct temporal intervals and the system is configured to be re-configured for different temporal adherence requirements depending on the device and medicament to be used.

6. The system of claim 1 comprising a module for identifying multiple inhalations; or an exhalation before inhalation after drug priming mechanism has been activated.

7. The system of claim 1 comprising a module for identifying insufficient inhalation volume to release the medication or delivery of the correct volume of the medication after drug priming mechanism has been activated.

8. The system of claim 1 wherein the processing circuitry comprises a module to identify different frequency components to differentiate between inhalations and exhalations to be used for user technique error identification.

9. The system of claim 1 comprising a module for comparing a zero crossing rate, a singular value decomposition of the short term power spectrum of the signal to a predefined threshold to identify potential breath sounds to be used for user technique error identification.

10. The system of claim 1 comprising a module for comparing a zero crossing rate, a singular value decomposition of the short term power spectrum of the signal to a predefined threshold to identify potential breath sounds to be used for user technique error identification wherein a zero crossing rate of the breath sounds is compared to a predefined threshold to confirm these as breath sounds using said comparing means.

11. The system of claim 1 wherein the signal is processed to determine the frequency domain components of the identified breath sounds and a module for classifying detected sounds as an inhalation or an exhalation.

12. The system of claim 1 wherein the processing circuitry comprises a module for tracking time of device inhaler use for adherence analysis.

13. The system of claim 1 comprising a module for calculating the median acoustic amplitude and duration of an identified inhalation to determine the amount of medicament released from the device.

14. The system of claim 1 comprising a module for calculating the amplitude of an identified exhalation in order to determine if the medicament has been dispersed from the inhaler, before inhalation has occurred.

15. The system of claim 1 comprising a module to calculate the minimum energy to disperse in the airways the medicament that has been achieved at exhalation.

16. The system of claim 1 comprising a module to calculate the duration of any breath sound.

17. The system of claim 1 comprising a module for recording and storing a time stamp indicating when the device is used.

18. The system of claim 1 comprising a module for recording after the inhaler is closed in order to identify exhalations after inhalation.

19. A computer implemented system for monitoring user technique of an inhaler device configured for delivery of a medicament, said system comprising:
  a module for processing a data signal obtained from a first microphone, wherein said data signal comprises acoustic information sensed,
  a module for processing a data signal obtained from a second microphone to determine inhalation or exhalation breath characteristics and/or cancel ambient noise,
  a module for determining inhalation and exhalation breath characteristics that occur during use of the inhaler, by analysing the temporal and spectral components of the acoustic information sensed; and
  a module for differentiating between an inhalation and an exhalation based on both the temporal and spectral components.

* * * * *